US010722407B2

(12) United States Patent
Jones et al.

(10) Patent No.: US 10,722,407 B2
(45) Date of Patent: Jul. 28, 2020

(54) ABSORBENT ARTICLE WITH PARTIAL LAMINATE WAIST ELASTIC MEMBER

(71) Applicant: Kimberly-Clark Worldwide, Inc., Neenah, WI (US)

(72) Inventors: Matthew Randall Jones, Appleton, WI (US); Robert Michael Hill, Jr., Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 389 days.

(21) Appl. No.: 15/518,805

(22) PCT Filed: Oct. 31, 2014

(86) PCT No.: PCT/US2014/063286
§ 371 (c)(1),
(2) Date: Apr. 13, 2017

(87) PCT Pub. No.: WO2016/068963
PCT Pub. Date: May 6, 2016

(65) Prior Publication Data
US 2017/0239106 A1 Aug. 24, 2017

(51) Int. Cl.
A61F 13/49 (2006.01)
A61F 13/496 (2006.01)
A61F 13/53 (2006.01)

(52) U.S. Cl.
CPC .... A61F 13/49011 (2013.01); A61F 13/4902 (2013.01); A61F 13/496 (2013.01); A61F 13/53 (2013.01); A61F 2013/530481 (2013.01)

(58) Field of Classification Search
CPC ............ A61F 13/49011; A61F 13/4902; A61F 13/496; A61F 13/53; A61F 2013/530481;
(Continued)

(56) References Cited

U.S. PATENT DOCUMENTS 4,352,355 A 10/1982 Mesek et al.
4,515,595 A 5/1985 Kievit et al.
(Continued)

FOREIGN PATENT DOCUMENTS

CN 101039804 A 9/2007
EP 0 119 827 B1 7/1988
(Continued)

Primary Examiner — Catharine L Anderson
Assistant Examiner — Lynne Anderson
(74) Attorney, Agent, or Firm — Kimberly-Clark Worldwide, Inc.

(57) ABSTRACT

An absorbent article (10) can include a waist elastic member (50, 150, 250). In one embodiment, the waist elastic member (50, 150, 250) can include a first longitudinal zone (92), a second longitudinal zone (94), and a middle longitudinal zone (93). The first longitudinal zone (92) can include a first elastic member (76) disposed between two layers of material, the second longitudinal zone (94) can include a second elastic member (78) disposed between two layers of material, and the middle longitudinal zone (93) can include less layers of materials than each of the first longitudinal zone (92) and the second longitudinal zone (94).

22 Claims, 6 Drawing Sheets

(58) Field of Classification Search
CPC .......... A61F 13/49466; A61F 13/49012; A61F 2013/49025; A61F 2013/49026; A61F 2013/49028; A61F 2013/4948
See application file for complete search history.

(56) References Cited

U.S. PATENT DOCUMENTS

| | | | |
|---|---|---|---|
| 4,968,313 A | 11/1990 | Sabee | |
| 5,034,008 A | 7/1991 | Breitkopf | |
| 5,151,092 A | 9/1992 | Buell et al. | |
| 5,242,436 A | 9/1993 | Weil et al. | |
| 5,451,219 A | 9/1995 | Suzuki et al. | |
| 5,576,090 A | 11/1996 | Suzuki | |
| 5,593,401 A * | 1/1997 | Sosalla | A61F 13/49011 604/385.28 |
| 5,716,478 A | 2/1998 | Boothe et al. | |
| 5,759,340 A | 6/1998 | Boothe et al. | |
| 5,827,259 A | 10/1998 | Laux et al. | |
| 6,869,494 B2 | 3/2005 | Roessler et al. | |
| 7,018,369 B2 | 3/2006 | VanGompel et al. | |
| 7,655,583 B2 | 2/2010 | Marche | |
| 8,052,665 B2 | 11/2011 | Wastlund-Karlsson et al. | |
| 8,377,027 B2 | 2/2013 | Hughes et al. | |
| 8,512,304 B2 | 8/2013 | Baba et al. | |
| 9,168,182 B2 * | 10/2015 | Hargett et al. | A61F 13/15699 |
| 2007/0038199 A1 | 2/2007 | Erdman et al. | |
| 2011/0251576 A1 | 10/2011 | Ando et al. | |

FOREIGN PATENT DOCUMENTS

| | | |
|---|---|---|
| WO | WO 2011/162652 A1 | 12/2011 |
| WO | WO 2014/004937 A1 | 1/2014 |

* cited by examiner

ABSORBENT ARTICLE WITH PARTIAL LAMINATE WAIST ELASTIC MEMBER

TECHNICAL FIELD

The present disclosure relates to absorbent articles.

BACKGROUND OF THE DISCLOSURE

Proper fitting of absorbent articles can provide a variety of benefits to the wearer of the article. For example, a proper fitting absorbent article can increase comfort of the absorbent article against the wearer's skin, improve the flexibility and range of motion of the wearer while wearing the absorbent article, and improve the gasketing of exudates.

To this end, absorbent articles can include various types of elastic components or features that help to provide enhanced fit of the article on wearer. One example of such an elastic feature is a waist elastic member. Some absorbent articles include one or more waist elastic members that are intended to provide a more customizable fit for the wearer around at least a portion of the waist circumference of the wearer. It is common for prior waist elastic members to have one or more elastic materials that are completely wrapped by a facing material, such that the ends of the facing material overlap one another and the facing material forms both a body facing side and garment facing side of the waist elastic member. In other prior waist elastic members, two separate materials can form the facings of the waist elastic member and laminate the elastic materials.

While prior waist elastic members have functioned adequately in absorbent articles, there is still a desire for improved flexibility of the waist elastic member to improve the fit of the absorbent article. Additionally, there is also a desire for increased softness of waist elastic member in an absorbent article, as in some forms, the waist elastic member may contact the wearer's skin.

SUMMARY OF THE DISCLOSURE

In one embodiment, an absorbent article can include a front waist region, a rear waist region, and a crotch region. The crotch region can extend between the front waist region and the rear waist region. The absorbent article can further include a longitudinal axis and a lateral axis. The absorbent article can include an absorbent assembly that includes a bodyside liner, an outer cover, and an absorbent body disposed between the bodyside liner and the outer cover. The bodyside liner can include a body facing surface and a garment facing surface. The outer cover can include a body facing surface and a garment facing surface. The absorbent article can further include a waist elastic member disposed in one of the front waist region and the rear waist region. The waist elastic member can include a body facing surface and a garment facing surface. The garment facing surface of the waist elastic member can be bonded to one of the bodyside liner and the outer cover. The waist elastic member can include a carrier sheet including a first surface, a second surface opposite from the first surface, a first lateral edge, a second lateral edge, and opposing end edges. The waist elastic member can further include a first elastic member and a second elastic member. The first elastic member and the second elastic member can each include a first side and a second side. The second side can be opposite from the first side. The first elastic member and the second elastic member can each be coupled to the second surface of the carrier sheet. The carrier sheet can be folded around the first elastic member such that a first portion of the carrier sheet is disposed on the first side of the first elastic member and a second portion of the carrier sheet is disposed on the second side of the first elastic member, where the second portion of the carrier sheet includes the first lateral edge. The carrier sheet can be folded such that the first lateral edge does not longitudinally extend to or longitudinally overlap the second lateral edge.

In another embodiment, an absorbent article can include a front waist region, a rear waist region, and a crotch region. The crotch region can extend between the front waist region and the rear waist region. The absorbent article can further include a longitudinal axis and a lateral axis. The absorbent article can include an absorbent assembly that includes a bodyside liner, an outer cover, and an absorbent body disposed between the bodyside liner and the outer cover. The bodyside liner can include a body facing surface and a garment facing surface. The outer cover can include a body facing surface and a garment facing surface. The absorbent article can further include a waist elastic member disposed in one of the front waist region and the rear waist region. The waist elastic member can include a body facing surface and a garment facing surface. The garment facing surface of the waist elastic member can be bonded to one of the bodyside liner and the outer cover. The waist elastic member can include a carrier sheet including a first surface, a second surface opposite from the first surface, a first lateral edge, a second lateral edge, and opposing end edges. The waist elastic member can further include a first laminating sheet including a first inner laminating surface, a first outer laminating surface opposite from the first inner laminating surface, a first edge, a second edge opposite the first edge, and opposing end edges. The first laminating sheet can be configured such that the first edge of the first laminating sheet substantially longitudinally aligns with the first lateral edge of the carrier sheet and the second edge of the first laminating sheet does not longitudinally extend to or overlap with the second lateral edge of the carrier sheet. The waist elastic member can also include a first elastic member and a second elastic member. The first elastic member and the second elastic member can each include a first side and a second side, the second side being opposite from the first side. The carrier sheet can be disposed on the first side of the first elastic member and the first side of the second elastic member. The first elastic member can be disposed between the second surface of the carrier sheet and the first inner laminating surface of the first laminating sheet.

In yet another embodiment, an absorbent article can include a front waist region, a rear waist region, and a crotch region. The crotch region can extend between the front waist region and the rear waist region. The absorbent article can further include a longitudinal axis and a lateral axis. The absorbent article can include a bodyside liner, an outer cover, and an absorbent body disposed between the bodyside liner and the outer cover. The bodyside liner can include a body facing surface and a garment facing surface. The outer cover can include a body facing surface and a garment facing surface. The absorbent article can further include a waist elastic member disposed in one of the front waist region and the rear waist region. The waist elastic member can include a body facing surface and a garment facing surface. The garment facing surface of the waist elastic member can be bonded to one of the bodyside liner and the outer cover. The waist elastic member can further include a first longitudinal zone, a second longitudinal zone, and a middle longitudinal zone in between the first longitudinal zone and the second longitudinal zone. The first longitudinal zone can include a first elastic member disposed between two layers of material. The second longitudinal zone can include a second elastic member disposed between two layers of material. The middle longitudinal zone can include less layers of material than each of the first longitudinal zone and the second longitudinal zone.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
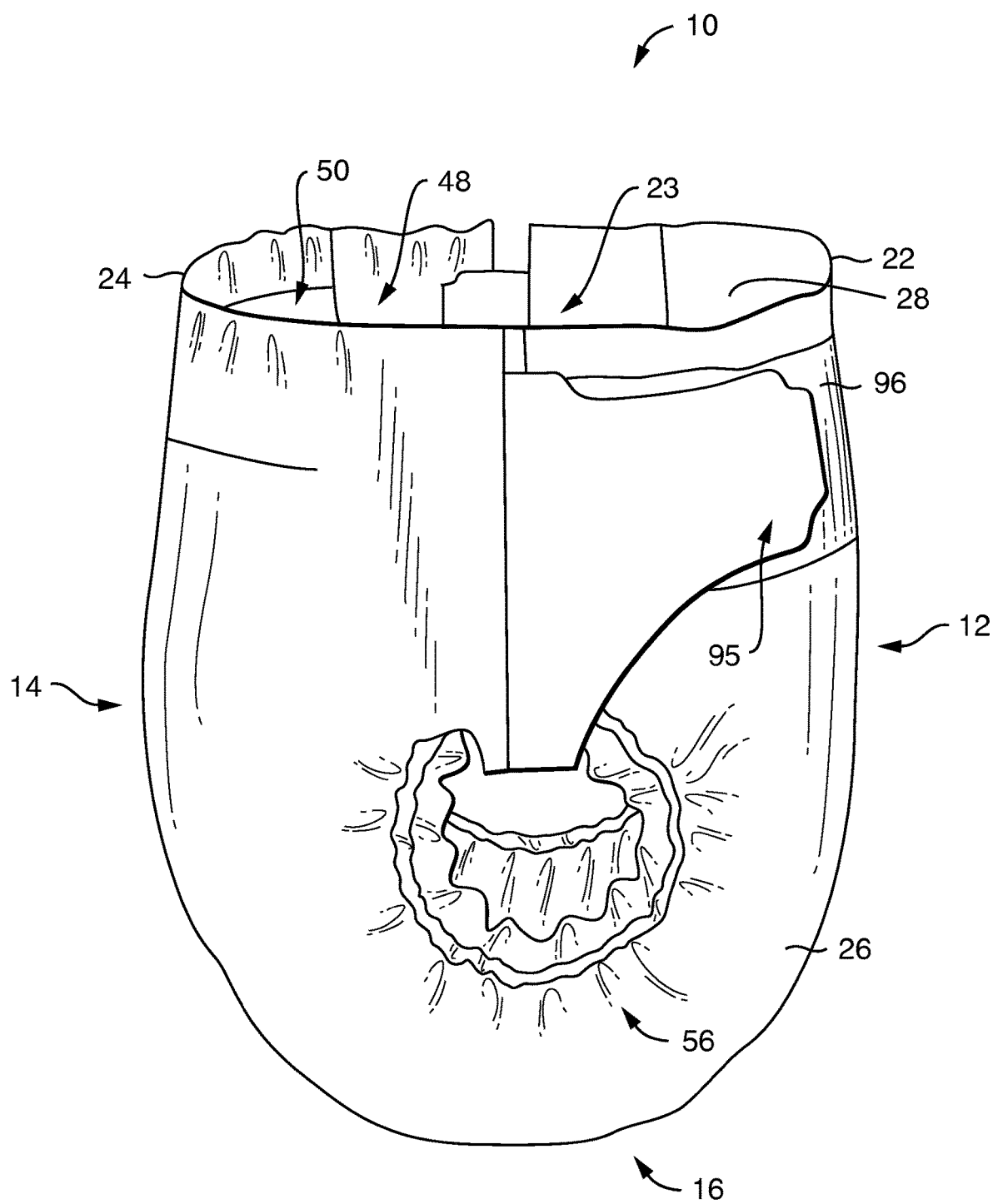
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISLOSURE

In an embodiment, the present disclosure is generally directed towards an absorbent article having a partial laminate waist elastic member. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user and a wearer can be one and the same person.

Figure 2:
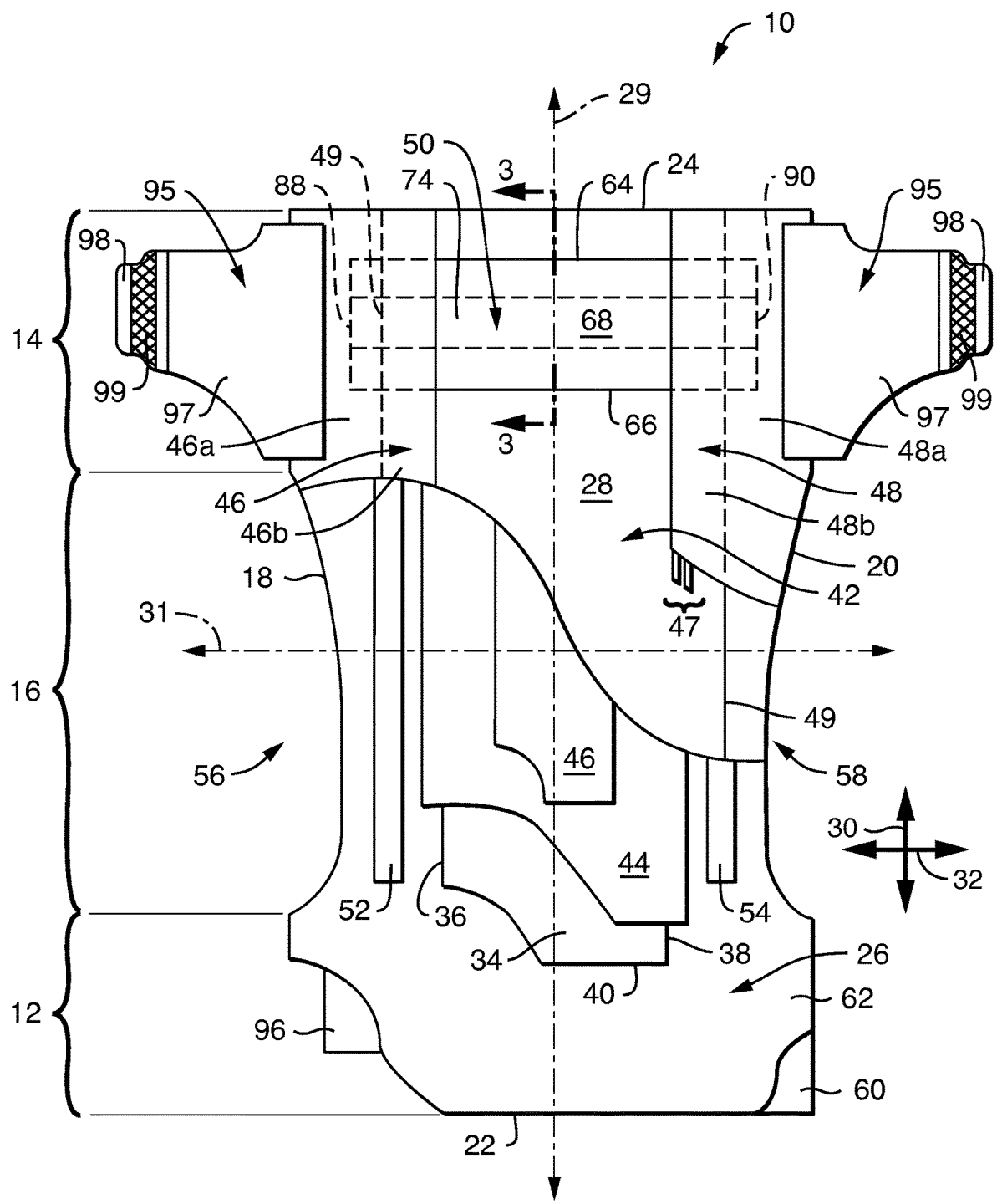
FIG. 2 is a top plan view of the absorbent article of FIG. 1 in a stretched, unfastened condition.

Absorbent Article:

Referring to FIGS. 1 and 2, a non-limiting illustration of an absorbent article 10, for example, a diaper, is illustrated. Other embodiments of the absorbent article could include training pants, youth pants, adult incontinence garments, and feminine hygiene articles. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define a central waist opening 23 for the waist of the wearer. Portions of the longitudinal side edges, 18 and 20, in the crotch region 16 can generally define leg openings for the legs of the wearer when the absorbent article 10 is worn.

The absorbent article 10 can include an outer cover 26 and a bodyside liner 28, the bodyside liner 28 being depicted in the cut-away portion of FIG. 1. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 1, the absorbent article 10 can have a longitudinal axis 29 extending in the longitudinal direction 30 and a lateral axis 31 extending in the lateral direction 32.

Figure 3:
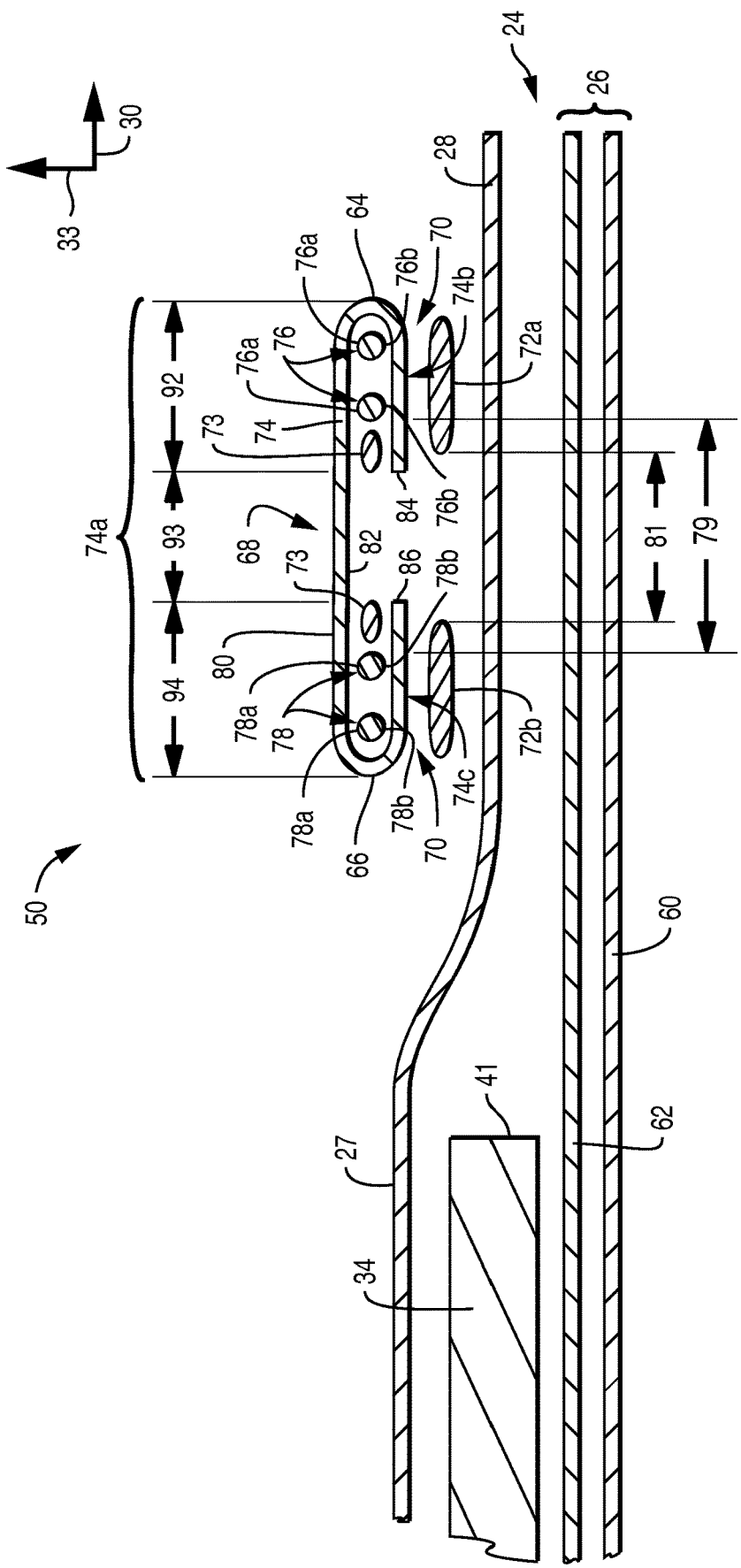
FIG. 3 is a cross-sectional view taken along line 3-3 from FIG. 2.

An absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have a first end edge 40 that is opposite a second end edge 41 (as shown in FIG. 3), respectively, which, in an embodiment, can form portions of the waist edges, 22 and 24, respectively, of the absorbent article 10. The first end edge 40 can be in the front waist region 12. The second end edge can be in the rear waist region 14. In an embodiment, the absorbent body 34 can have a length and width that are the same as or less than the length and width of the absorbent article 10. The bodyside liner 28, the outer cover 26, and the absorbent body 34 can form part of an absorbent assembly 42. The absorbent assembly 42 can also include a fluid transfer layer 44 and a fluid acquisition layer 46.

The absorbent article 10 can be configured to contain and/or absorb liquid, solid, and semi-solid body exudates discharged from the wearer. In one embodiment, containment flaps 46, 48, can be configured to provide a barrier to the lateral flow of body exudates. To further enhance containment and/or absorption of body exudates, in some embodiments the absorbent article 10 can suitably include a waist elastic member, such as a rear waist elastic member 50. Additionally and/or alternatively, the absorbent article 10 can include a front waist elastic member, although one is not depicted herein. The absorbent article 10 can further include leg elastic members 52, 54 as are known to those skilled in the art. The leg elastic members 52, 54 can be attached to the outer cover 26 and/or the bodyside liner 28 along the opposite longitudinal side edges, 18 and 20, and positioned in the crotch region 16 of the absorbent article 10. The leg elastic members 52, 54, can be parallel to the longitudinal axis 29 as shown in FIG. 2, or can be curved as is known in the art. The leg elastic members 52, 54 can provide elasticized leg cuffs 56, 58.

Additional details regarding each of these elements of the absorbent article 10 described herein can be found below and with reference to the FIGS. 1 through 6.

Outer Cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In an embodiment, such as that shown in FIGS. 1 and 2, the outer cover 26 can be a two layer construction, including an outer layer 60 material and an inner layer 62 material which can be bonded together such as by a laminate adhesive. Suitable laminate adhesives can be applied continuously or intermittently as beads, a spray, parallel swirls, or the like, but it is to be understood that the inner layer 62 can be bonded to the outer layer 60 by other bonding methods, including, but not limited to, ultrasonic bonds, thermal bonds, pressure bonds, or the like.

The outer layer 60 of the outer cover 26 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer 60 of an outer cover 26 can be a 20 gsm spunbond polypropylene non-woven web. The outer layer 60 may also be constructed of the same materials from which the bodyside liner 28 can be constructed as described herein.

The liquid impermeable inner layer 62 of the outer cover 26 (or the liquid impermeable outer cover 26 where the outer cover 26 is of a single-layer construction) can be either vapor permeable (i.e., "breathable") or vapor impermeable. The liquid impermeable inner layer 62 (or the liquid impermeable outer cover 26 where the outer cover 26 is of a single-layer construction) can be manufactured from a thin plastic film. The liquid impermeable inner layer 62 (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. In one embodiment, FIG. 2 illustrates an absorbent body 34 that is rectangular in shape. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

The absorbent body 34 can be superposed over the inner layer 62 of the outer cover 26 and can be bonded to the inner layer 62 of the outer cover 26, such as by being bonded thereto with adhesive. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In an embodiment, such as that illustrated in FIG. 2, a layer, such as but not limited to, a fluid transfer layer 44, can be positioned between the absorbent body 34 and the outer cover 26. The absorbent body 34 can be bonded to the fluid transfer layer 44.

Bodyside Liner:

The bodyside liner 28 of the absorbent article 10 can overlay the absorbent body 34 and the outer cover 26 and can isolate the wearer's skin from liquid waste retained by the absorbent body 34.

In various embodiments, a fluid transfer layer 44 can be positioned between the bodyside liner 28 and the absorbent body 34. In various embodiments, an acquisition layer 46 can be positioned between the bodyside liner 28 and the absorbent body 34 or a fluid transfer layer 44, if present. In various embodiments, the bodyside liner 28 can be bonded to the acquisition layer 46, or to the fluid transfer layer 44 if no acquisition layer 46 is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 44, if present, and/or an acquisition layer 46, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. The bodyside liner 28 may be narrower than the outer cover 26, but it is to be understood that the bodyside liner 28 and the outer cover 26 may be of the same dimensions, or that the bodyside liner 28 may be of greater width than the outer cover 26. It is also contemplated that the bodyside liner 28 may not extend beyond the absorbent body 34 and/or may not be secured to the outer cover 26. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Figure 5:
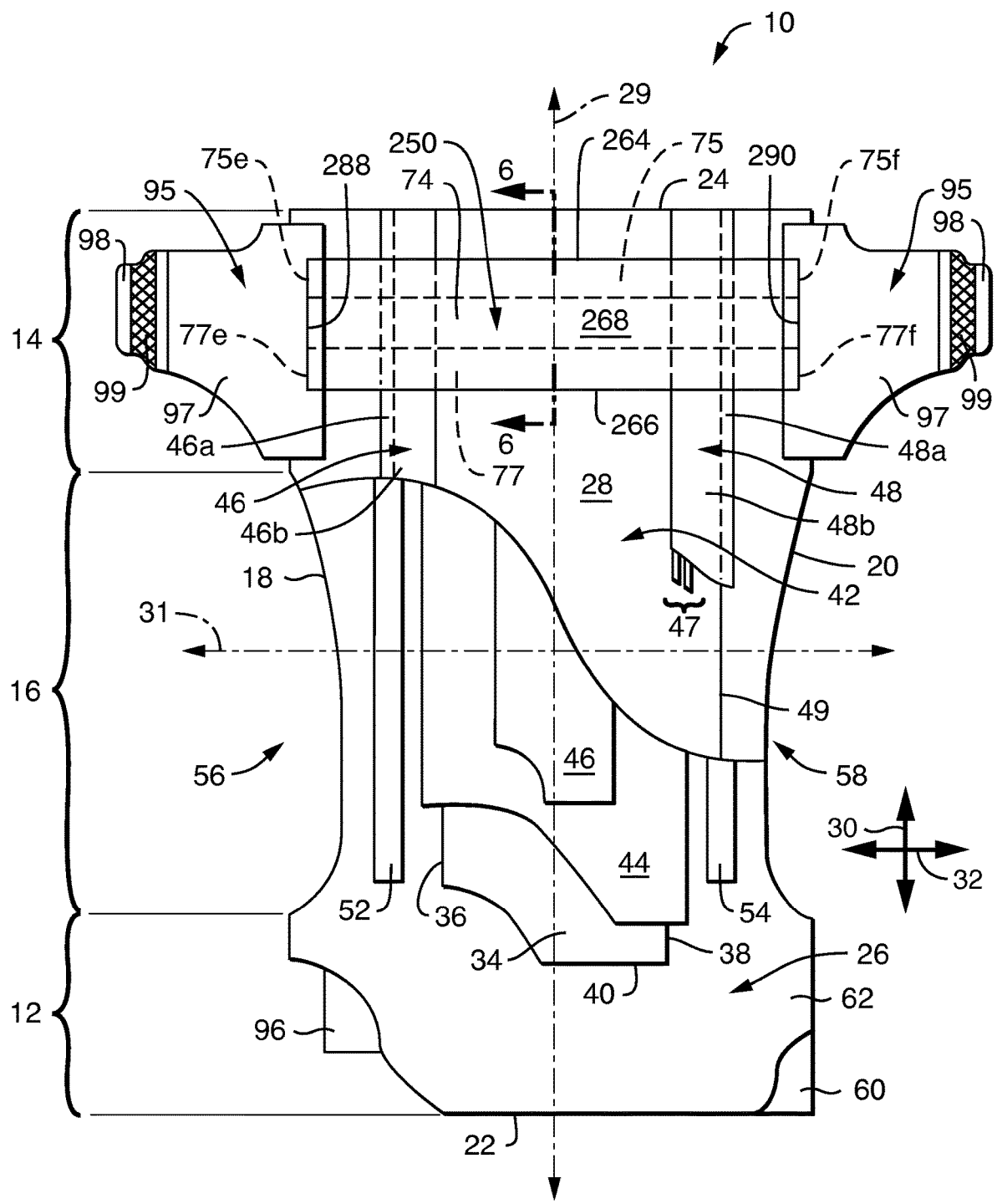
FIG. 5 is a top plan view of yet another alternative embodiment of an absorbent article, such as a diaper, in a stretched, unfastened condition.

Containment Flaps:

In an embodiment, containment flaps 46, 48 can be secured to the body facing liner 28 of the absorbent article 10 in a generally parallel, spaced relation with each other laterally inward of the leg openings to provide a barrier against the flow of body exudates. In an embodiment, the containment flaps 46, 48 can extend longitudinally from the front waist region 12 of the absorbent article 10, through the crotch region 16 to the back waist region 14 of the absorbent article 10. The containment flaps 46, 48 can be bonded to the body facing liner 28 with a barrier adhesive 49, as shown in FIGS. 2 and 5, or other suitable means. Alternatively, each containment flap 46, 48 can be bonded to other components of the absorbent article 10 other than the body facing liner 28, including, but not limited to, the backsheet 26. The containment flaps 46, 48 can be constructed of a fibrous material which can be similar to the material forming the body facing liner 28. Other conventional materials, such as polymer films, can also be employed.

In some embodiments, as illustrated in FIGS. 2 and 5, the containment flaps 46, 48 can each include a proximal end 46a, 48a, respectively, that is bonded to the bodyside liner 28 with a barrier adhesive 49. In some embodiments, such as the embodiment illustrated in FIG. 2, the proximal ends 46a, 48a can laterally extend to the respective longitudinal side edges 18, 20 of the absorbent article 10. In other embodiments, such as the embodiment illustrated in FIG. 5, the proximal ends 46a, 48 do can end laterally inward of the respective longitudinal side edges 18, 20 of the absorbent article 10. The containment flaps 46, 48 can also each include a distal end 46b, 48b, respectively, that can be moveable with respect to the absorbent assembly 42 in at least the crotch region 16. The containment flaps 46, 48 can include flap elastics, such as the two flap elastics 47 depicted in containment flap 48 in FIGS. 2 and 5. The containment flap 46 can be configured in the same manner as containment flap 48 discussed and illustrated herein. Suitable elastic materials for the flap elastics 47, can include sheets, strands or ribbons of natural rubber, synthetic rubber, or thermoplastic elastomeric materials.

The flap elastics 47, as illustrated in FIGS. 2 and 5, can have two strands of elastomeric material extending longitudinally along the distal end 48b of the containment flap 48, in generally parallel, spaced relation with each other. The elastic strands can be within the containment flap 48 while in an elastically contractible condition such that contraction of the strands gathers and shortens the distal ends 48b of the containment flap 48. As a result, the elastic strands can bias the distal end 48b of the containment flap 48 toward a position spaced from the proximal end 48a of the containment flap 48, so that the containment flap 48 can extend away from the body facing liner 28 in a generally upright orientation of the containment flaps 48, especially in the crotch region 16 of the absorbent article 10, when the absorbent article 10 is fitted on the wearer. As stated above, the containment flap 46 can be configured in the same manner as containment flap 48 discussed and illustrated herein, and thus, the distal end 46b of containment flap 46 can extend away from the body facing liner 28 in a similar manner. The distal end 48b of the containment flap 48 can be connected to the flap elastics 47, by partially doubling the containment flap 48 material back upon itself by an amount which can be sufficient to enclose the flap elastics 47. It is to be understood, however, that the containment flaps, 46 and 48, can have any number of strands of elastomeric material and may also be omitted from the absorbent article 10 without departing from the scope of this disclosure.

Leg Elastics:

Leg elastic members 52, 54 (labeled in FIGS. 2 and 5) can be secured to the outer cover 26, such as by being bonded thereto by laminate adhesive, generally laterally inward of the longitudinal side edges, 18 and 20, of the absorbent article 10. The leg elastic members 52, 54 can form elasticized leg cuffs 56, 58, respectively, that further help to contain body exudates. In an embodiment, the leg elastic members 52, 54 may be disposed between the inner layer 62 and outer layer 60 of the outer cover 26 or between other layers of the absorbent article 10. The leg elastic members 52, 54 can be a single elastic member as illustrated herein, or each leg elastic member 52, 54 can include more than one elastic member. A wide variety of elastic materials may be used for the leg elastic members 52, 54. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Of course, the leg elastic members 52, 54 can be omitted from the absorbent article 10 without departing from the scope of this disclosure.

Waist Elastic Members:

In an embodiment, the absorbent article 10 can have one or more waist elastic members 50, 150, 250. The waist elastic member 50, 150, 250 can be disposed in the rear waist region 14 as illustrated in FIGS. 1-6. In some embodiments, the absorbent article 10 can have a waist elastic member disposed in the front waist region 12. In other embodiments, the absorbent article 10 can have a waist elastic member in both the rear waist region 14 and the front waist region 12.

As illustrated in FIG. 1-6, the waist elastic member 50, 150, 250 can be disposed in the rear waist region 14. The waist elastic member 50 of FIGS. 2 and 3 can include an upper edge 64 and a lower edge 66, with the upper edge 64 being further from the lateral axis 31 than is the lower edge 66. In some embodiments, the upper edge 64 can be closer to the rear waist edge 24 than is the lower edge 66. The waist elastic member 50 can include a body facing surface 68 and a garment facing surface 70. Similarly, the waist elastic member 150 of FIG. 4 can include an upper edge 164 and a lower edge 166, and a body facing surface 168 and a garment facing surface 170. The waist elastic member 250 of FIGS. 5 and 6 can include an upper edge 264 and a lower edge 266, and a body facing surface 268 and a garment facing surface 270. The waist elastic members 50, 150, 250 can be configured such that the upper edge 64, 164, 264, is longitudinally offset from the rear waist edge 24 of the absorbent article 10.

The waist elastic member 50, 150, 250 can be bonded to the absorbent assembly 42. The garment facing surface 70 of the waist elastic member 50 can be bonded to one of the body facing liner 28 and the outer cover 26. In some embodiments, such as in the embodiment illustrated in FIGS. 2 and 3, the garment facing surface 70 of the waist elastic member 50 can be disposed on the body facing surface 27 of the bodyside liner 28 and the garment facing surface 70 can be bonded to the bodyside liner 28. As depicted in FIG. 2, the containment flaps 46, 48 can be bonded to the body facing surface 68 of the waist elastic member 50 such that the waist elastic member 50 is disposed between the containment flaps 46, 48 and the body facing surface 27 of the bodyside liner 28. However, in an alternative embodiment, such as the embodiment depicted in FIG. 4, the waist elastic member 150 can be disposed between the bodyside liner 28 and the outer cover 26 and the garment facing surface 170 of the waist elastic member 150 can be bonded to the body facing surface 25 of the outer cover 26.

Figure 4:
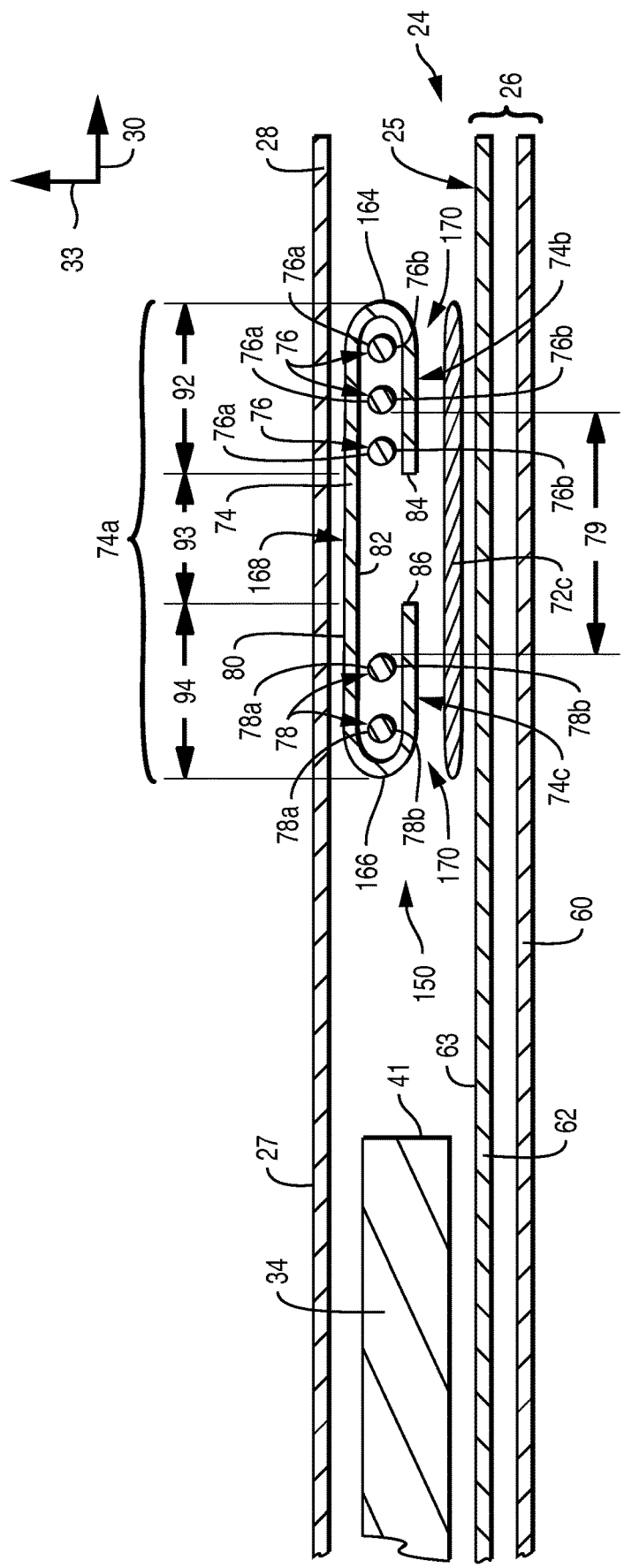
FIG. 4 is a cross-sectional view similar to FIG. 3 illustrating an alternative embodiment.
Figure 6:
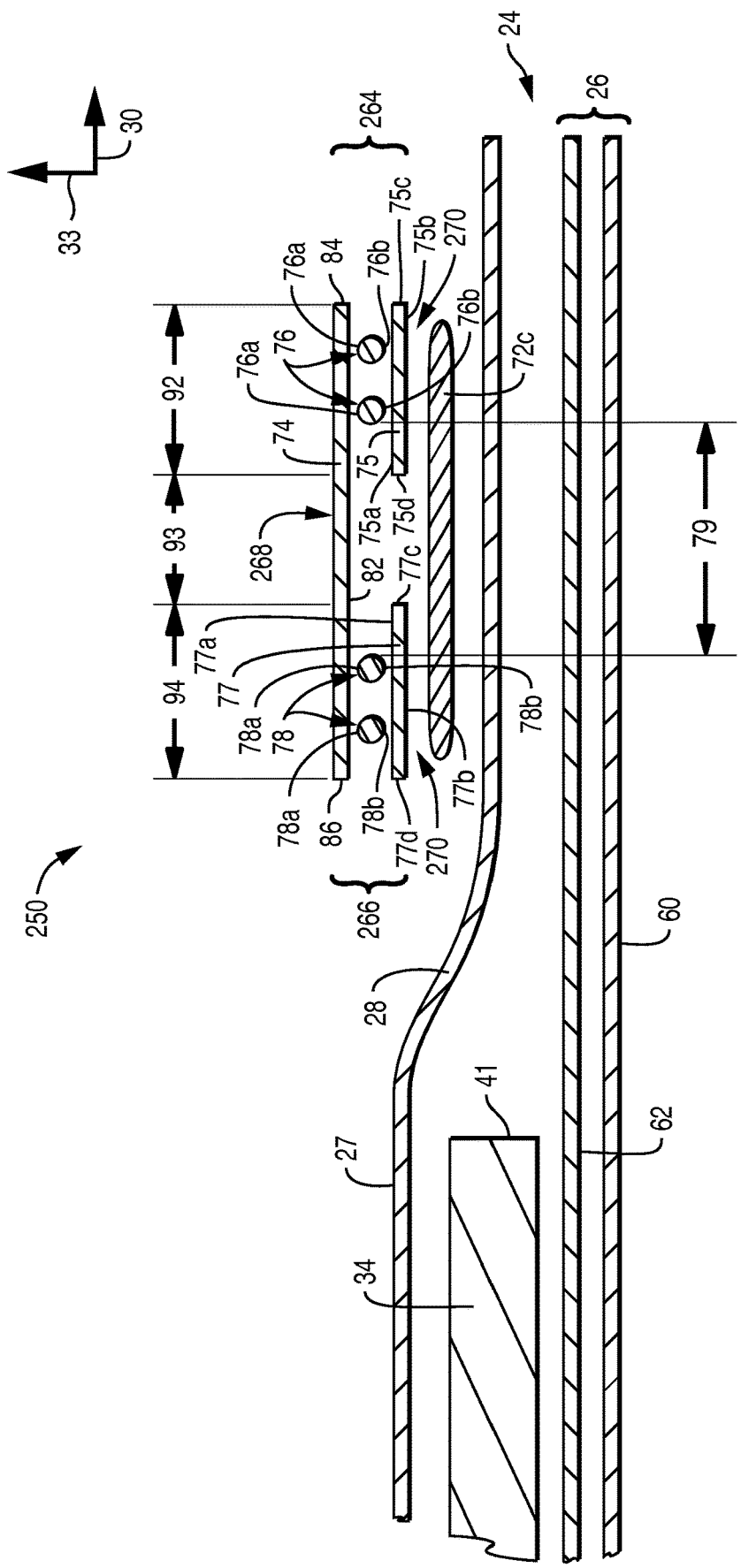
FIG. 6 is a cross-sectional view taken along line 6-6 from FIG. 5.

In some embodiments, such as the embodiments depicted in FIGS. 4 and 6, substantially all of the garment facing surface 170, 270 of the waist elastic member 150, 250 can be bonded to the absorbent assembly 42. In the embodiment depicted in FIG. 4, the body facing surface 25 of the outer cover 26 can be the body facing surface 63 of the inner layer 62 of the outer cover 26. The garment facing surface 170 of the waist elastic member 150 of FIG. 4 can be bonded to the bodyside liner 28 with adhesive 72c. In the embodiment depicted in FIG. 6, the garment facing surface 270 of the waist elastic member 250 is bonded to the body facing surface 27 of the bodyside liner 28 with adhesive 72c.

In other embodiments, not substantially all of the garment facing surface 70 of the waist elastic member 50 is bonded to the absorbent assembly 42. The garment facing surface 70 of the waist elastic member 50 of FIG. 3 can be bonded to the bodyside liner 28 with adhesive 72a, 72b. Of course, it can be appreciated that the waist elastic member 50 of FIGS. 2 and 3 could be configured to be bonded to the body facing surface 27 of the bodyside liner 28 with adhesive 72c such as shown in FIGS. 4 and 6 such that substantially all of the garment facing surface 70 of the waist elastic member 50 is bonded to the bodyside liner 28. Similarly, it can be appreciated that the waist elastic member 150 of FIG. 4 could be configured to be bonded to the outer cover 26 and the waist elastic member 250 of FIG. 6 could be configured to be bonded to the bodyside liner 28 with adhesives 72a and 72b such as shown in FIG. 3 such that not substantially all of the garment facing surface 170 of the waist elastic member 150 is bonded to the outer cover 26 and such that not all of the garment facing surface 270 of the waist elastic member 250 is bonded to the bodyside liner 28. Of course, it is also contemplated that the waist elastic members 50, 150, 250 can be bonded to the absorbent assembly 42 with suitable means other than adhesives, 72a, 72b, 72c, such as pressure bonding, ultrasonic bonding, thermal bonding, stitching, and any other suitable means.

As illustrated in FIGS. 3 and 4, the waist elastic member 50, 150 can include a carrier sheet 74, a first elastic member 76, and a second elastic member 78. The carrier sheet 74 can include a first surface 80 and a second surface 82. The second surface 82 can be opposite from the first surface 80. The carrier sheet 74 can also include a first lateral edge 84 and a second lateral edge 86. As shown in FIG. 2, the carrier sheet 74 can also include opposing end edges 88, 90. In some embodiments, the carrier sheet 74 can be a non-woven. In some embodiments, the carrier sheet 74 can be a spunbond-metlblown-spunbond ("SMS") material. In some embodiments, the carrier sheet 74 can be a spunbond material. In preferable embodiments, the carrier sheet 74 can have a basis weight from about 8 to about 20 grams per square meter (GSM). Of course, the carrier sheet 74 can be comprised of other materials other than the preferable materials listed above and have a basis weight outside the preferable range listed herein.

The waist elastic member 50, 150, 250 can also include a first elastic member 76 and a second elastic member 78. The first elastic member 76 and the second elastic member 78 can include one or more elastic materials. For example, the first elastic member 76 and the second elastic member 78 in the embodiments in FIGS. 3 and 6 each include two elastic materials. In the embodiment depicted in FIG. 4, however, the first elastic member 76 is depicted as having three elastic materials and the second elastic member 78 is depicted as having two elastic materials. Thus, the first elastic member 76 and the second elastic member 78 can have different numbers of elastic materials than one another. Suitable elastic materials for the first elastic member 76 and the second elastic member 78 of the waist elastic members 50, 150 can include, but are not limited to, sheets, strands or ribbons of natural rubber, synthetic rubber, or thermoplastic elastomeric polymers. In a preferred embodiment, the elastic materials for the first elastic member 76 and the second elastic member 78 can be spandex, such as a Lycra® spandex.

The first elastic member 76 includes a first side 76a and a second side 76b that is opposite the first side 76a. Similarly, the second elastic member 78 includes a first side 78a and a second side 78b that is opposite the first side 78a. In the embodiments depicted in FIGS. 3, 4, and 6, the first side 76a of the first elastic member 76 and the first side 78a of the second elastic member 78 are each configured to face the body of the wearer. The elastic materials of the first and second elastic members 76, 78 can be stretched and bonded to the carrier sheet 74, bonded to a gathered carrier sheet 74, or bonded to the carrier sheet 74 and then elasticized or shrunk, for example, with the application of heat, such that elastic retractive forces are imparted to the carrier sheet 74, and thus, the waist elastic member 50, 150, 250. As illustrated in the embodiments in FIGS. 3, 4 and 6, the first elastic member 76 and the second elastic member 78 can each be coupled to the second surface 82 of the carrier sheet 74.

In some embodiments, such as the embodiments of the waist elastic members 50, 150 illustrated in FIGS. 3 and 4, the carrier sheet 74 is folded around the first elastic member 76 such that a first portion 74a of the carrier sheet 74 is disposed on the first side 76a of the first elastic member 76 and a second portion 74b of the carrier sheet 74 is disposed on the second side 76b of the first elastic member 76. The first portion 74a of the carrier sheet 74 can extend from the upper edge 64 of the waist elastic member 50 to the lower edge 66 of the waist elastic member 50 as shown in FIG. 3, and from the upper edge 164 of the waist elastic member 150 to the lower edge 166 of the waist elastic member 150 as shown in FIG. 4. The second portion 74b of the carrier sheet 74 can extend from the upper edge 64 of the waist elastic member 50 to the first lateral edge 84 of the carrier sheet 74 as shown in FIG. 3, and from the upper edge 164 of the waist elastic member 150 to the first lateral edge 84 of the carrier sheet 74 as shown in FIG. 4.

Additionally, the carrier sheet 74 can be folded around the second elastic member 78 such that the first portion 74a of the carrier sheet is disposed on the first side 78a of the second elastic member 78 and a third portion 74c of the carrier sheet 74 is on the second side 78b of the second elastic member 78. The third portion 74c of the carrier sheet 74 can extend from the lower edge 66 of the waist elastic member 50 to the second lateral edge 86 of the carrier sheet 74 as shown in FIG. 3, and from the lower edge 166 of the waist elastic member 150 to the second lateral edge 86 of the carrier sheet 74 as shown in FIG. 4. As illustrated in FIG. 3, the second surface 82 of the carrier sheet 74 in the second portion 74b of the carrier sheet 74 near the first lateral edge 84 can be bonded to the second surface 82 of the carrier sheet 74 in the first portion 74a of the carrier sheet 74 between the first elastic member 76 and the second elastic member 78 with a barrier adhesive 73. The second surface 82 of the carrier sheet 74 in the third portion 74c of the carrier sheet 74 near the second lateral edge 86 can be bonded to the second surface 82 of the carrier sheet 74 in the first portion 74a of the carrier sheet 74 between the first elastic member 76 and the second elastic member 78 with a barrier adhesive 73.

In folding around the first elastic member 76, the first lateral edge 84 of the carrier sheet 74 does not longitudinally extend to or longitudinally overlap the second lateral edge 86 of the carrier sheet 74. In other words, for an embodiment located internal to the rear waist edge 24, the distance between the first lateral edge 84 and the rear waist edge 24 is less than the distance between the second lateral edge 86 and the rear waist edge 24. Folding the carrier sheet 74 around the first elastic member 76 in this manner provides a partial laminate waist elastic, providing advantages as will be discussed in more detail below. In folding around the second elastic member 78, the second lateral edge 86 of the carrier sheet 74 does not longitudinally extend to or longitudinally overlap the first lateral edge 84 of the carrier sheet 74. Similar to the discussion above regarding folding the carrier sheet 74 around the first elastic member 76, folding the carrier sheet 74 around second elastic member 78 as noted above provides that the distance between the first lateral edge 84 and the rear waist edge 24 is less than the distance between the second lateral edge 86 and the rear waist edge 24. Folding the carrier sheet 74 around the second elastic member 78 in this manner provides a partial laminate waist elastic, providing advantages as will be discussed in more detail below.

FIGS. 5 and 6 depict another embodiment of a waist elastic member 250. In FIG. 5, the waist elastic member 250 is depicted as being disposed on the body facing surface 27 of the bodyside liner 28 and above the containment flaps 46, 48 such that the garment facing surface 270 of the waist elastic member 250 is bonded to the body facing surface 27 of the bodyside liner 28 and the containment flaps 46, 48. As depicted in FIG. 6, the garment facing surface 270 of the waist elastic member 250 can be bonded to the body facing surface 27 of the bodyside liner 28 and the containment flaps 46, 48 with adhesive 72c. As noted above, it can be appreciated that the waist elastic member 250 can be bonded to the body facing surface 27 of the bodyside liner 28 and the containment flaps 46, 48 with adhesives 72a and 72b as shown in FIG. 3 and as discussed above. Furthermore, it can be appreciated, that the waist elastic member 250 could alternatively be configured to be disposed between the bodyside liner 28 and the outer cover 26. For example, the garment facing surface 270 of the waist elastic member 250 could be bonded to the inner layer 62 of the outer cover 26, as described above with respect to the configuration of the waist elastic member 150 and as illustrated in FIG. 4.

As illustrated in FIG. 6, the waist elastic member 250 can include a carrier sheet 74. The waist elastic member 250 can further include a first laminating sheet 75. In some embodiments, such as the embodiment illustrated in FIG. 6, the waist elastic member 250 can also include a second laminating sheet 77. In some embodiments, the first laminating sheet 75 can be comprised of the same material as the second laminating sheet 77. In some embodiments, the first laminating sheet 75 can be comprised of a different material as the second laminating sheet 77. The first and second laminating sheets 75, 77, respectively, can be comprised of the same or different materials as the carrier sheet 74.

The first laminating sheet 75 and the second laminating sheet 77 can each include an inner laminating surface 75a, 77a, respectively, and an outer laminating surface 75b, 77b, respectively. The inner laminating surface 75a of the first laminating sheet 75 can be opposite from the outer laminating surface 75b of the first laminating sheet 75. Similarly, the inner laminating surface 77a of the second laminating sheet 77 can be opposite from the outer laminating surface 77b of the second laminating sheet 77. The first laminating sheet 75 and the second laminating sheet 77 can each include a first edge 75c, 77c, respectively, and a second edge 75d, 77d. The first edge 75c of the first laminating sheet 75 can be opposite from the second edge 75d of the first laminating sheet 75. Similarly, the first edge 77c of the second laminating sheet 77 can be opposite from the second edge 77c of the second laminating sheet 77. The first laminating sheet 75 can include opposing end edges 75e, 75f and the second laminating sheet 77 can also include opposing end edges 77e, 77f, as illustrated in FIG. 5.

The waist elastic member 250 can also include a first elastic member 76. In some embodiments, such as the embodiment illustrated in FIG. 6, the waist elastic member 250 can include a second elastic member 78. The carrier sheet 74 can be disposed on the first side 76a of the first elastic member 76 and the first side 78a of the second elastic member 78. The first elastic member 76 can be disposed between the second surface 82 of the carrier sheet 74 and the inner laminating surface 75a of the first laminating sheet 75. The second elastic member 78 can be disposed between the second surface 82 of the carrier sheet 74 and the inner laminating surface 77a of the second laminating sheet 77.

As further illustrated in FIG. 6, the first laminating sheet 75 can be configured such that the first edge 75c of the first laminating sheet 75 substantially longitudinally aligns with the first lateral edge 84 of the carrier sheet 74 and the second edge 75d of the first laminating sheet 75 does not longitudinally extend to or overlap with the second lateral edge 86 of the carrier sheet 74. In other words, the distance between the second edge 75d of the first laminating sheet 75 and the rear waist edge 24 is less than the distance between the second lateral edge 86 of the carrier sheet 74 and the rear waist edge 24, providing a partial laminate waist elastic. Additionally, the second laminating sheet 77 can be configured such that the second edge 77d of the second laminating sheet 77 substantially longitudinally aligns with the second lateral edge 86 of the carrier sheet 74 and the first edge 77c of the second laminating sheet 77 does not longitudinally extend to or overlap with the second edge 75d of the first laminating sheet 75. In other words, the distance between the second edge 75d of the first laminating sheet 75 and the rear waist edge 24 is less than the distance between the first edge 77c of the second laminating sheet 77 and the rear waist edge 24. In such a configuration, the waist elastic member 250 can provide a partial laminate waist elastic.

The embodiments of the waist elastic members 50, 150, 250 as depicted in FIGS. 3, 4, and 6 each provide a first longitudinal zone 92, a second longitudinal zone 94, and a middle longitudinal zone 93 in between the first and second longitudinal zones 92, 94. The longitudinal zones 92, 93, 94 discussed herein are distinguishing three different regions of the waist elastic members 50, 150, 250 in the longitudinal direction 30. Each of the longitudinal zones 92, 93, 94 include the full depth of the waist elastic members 50, 150, 250 in a direction 33 perpendicular to both the longitudinal and lateral directions 30, 32.

The first longitudinal zone 92 can include the first elastic member 76 disposed between two layers of material. For example, in the waist elastic members 50, 150 of FIGS. 3 and 4, respectively, the first elastic member 76 can be disposed between two layers of material provided by the carrier sheet 74. Specifically, the first portion 74a of the carrier sheet 74 can provide a first layer of material and the second portion 74b of the carrier sheet 74 can provide a second layer of material in the first longitudinal zone 92. In the embodiment depicted in FIG. 6, the waist elastic member 250 can include the first elastic member 76 disposed between a first layer of material that can be provided by the carrier sheet 74 and a second layer of material that can be provided by the first laminating sheet 75 in the first longitudinal zone 92.

The second longitudinal zone 94 can include the second elastic member 78 disposed between two layers of material. For example, in the waist elastic members 50, 150 of FIGS. 3 and 4, respectively, the second elastic member 78 can be disposed between two layers of the carrier sheet 74. Specifically, the first portion 74a of the carrier sheet 74 can provide the first layer of material and the third portion 74c of the carrier sheet 74c can provide the second layer of material in the second longitudinal zone 94. In the embodiment depicted in FIG. 6, the waist elastic member 250 can include the second elastic member 78 disposed between a first layer of material that can be provided by the carrier sheet 74 and a second layer of material that can be provided by the second laminating sheet 77 in the second longitudinal zone 94.

As shown in the embodiments depicted in FIGS. 3, 4, and 6, the middle longitudinal zone 93 can include less layers than each of the first longitudinal zone 92 and the second longitudinal zone 94. The middle longitudinal zone 93 can be configured such that it does not include an elastic member. The middle longitudinal zone 93 can include a first layer of material provided by the carrier sheet 74, such as shown in FIGS. 3, 4, and 6. As shown in the embodiments depicted in FIGS. 3 and 4, the carrier sheet 74 can be folded as described above such that the second portion 74b of the carrier sheet 74 and the third portion 74c of the carrier sheet 74 are not within the middle longitudinal zone 93 of the waist elastic member 50, 150. In the embodiment illustrated in FIG. 6, the waist elastic member 250 is configured such that the first laminating sheet 75 and the second laminating sheet 77 are not within the middle longitudinal zone 93.

By having less layers in the middle longitudinal zone 93 as compared to each of the first and second longitudinal zones 92, 94, respectively, the waist elastic member 50, 150, 250 can provide a partial laminate waist elastic, which can provide advantages over prior waist elastics that are complete laminates. As an example, the waist elastic member 50, 150, 250 can be more flexible due to less layers of material being in the middle longitudinal zone 93 as compared to each of the first and second longitudinal zones 92, 94, respectively. As such, the waist elastic member 50, 150, 250 can aid in maintaining its position on the wearer when the wearer bends or moves at the wearer's waist. Additionally, if the carrier sheet 74 and/or the first laminating sheet 75 and/or the second laminating sheet 77 are comprised of opaque materials, the waist elastic material 50, 150, 250 can provide an aesthetic of a "two-tiered" waist elastic member 50, 150, 250 by having more opacity in the first longitudinal zone 92 and the second longitudinal zone 94 as compared to the middle longitudinal zone 93. This "two-tiered" aesthetic to the waist elastic member 50, 150, 250 can help portray one or more benefits of the waist elastic member 50, 150, 250 to the caregiver.

In some embodiments, such as the embodiments depicted in FIGS. 3, 4, and 6, the waist elastic members 50, 150, 250 can each include a longitudinal gap 79 between the first elastic member 76 and the second elastic member 78. In some embodiments where the first and/or second elastic members 76, 78, respectively, include more than one elastic material, the longitudinal gap 79 can be greater than the longitudinal spacing between individual elastic materials in the first and/or second elastic members 76, 78, respectively. In some embodiments, the waist elastic member 50 can be configured such that the longitudinal gap 79 generally aligns with a central unbonded region 81 of the waist elastic member 50, such as illustrated in FIG. 3. By providing a space between adhesives 72a and 72b, the waist elastic member 50 in the central unbonded region 81 can move relative to the absorbent assembly 42. The central unbonded region 81 can provide additional flexibility to the waist elastic member 50, increased softness to the waist elastic member 50 by not having adhesive or other bonding means in the central unbonded region 81, and cost savings by reducing the adhesive used to couple the waist elastic member 50 to the absorbent assembly 42.

The first elastic member 76 and the second elastic member 78 can be provided in a variety of configurations in the waist elastic member 50, 150, 250. For example, in some embodiments, the decitex of the first elastic member 76 can be different than the decitex of the second elastic member 78. As one example, the decitex of the second elastic member 78 can be greater than the decitex of the first elastic member 76. As a result, the second elastic member 78 can provide more contractive force than the first elastic member 76 and help follow the curves of the wearer's body. In various embodiments, it is preferred that the decitex of the first elastic member 76 and the second elastic member can be between about 470 to about 1200. Of course, it is contemplated that the decitex of the first and second elastic members 76, 78 can be outside of this preferable range. It is also contemplated that the decitex can be the same for the first elastic member 76 and the second elastic member 78.

Additionally and/or alternatively, an elongation amount of the first elastic member 76 can be different than an elongation amount of the second elastic member 78. For example, in some embodiments, the elongation amount of the second elastic member 78 can be greater than the elongation amount of the first elastic member 76. Such a difference between the elongation of the second elastic member 78 and the first elastic member 76 can help provide an improved fit on the wearer's body due to higher contractive forces in the second elastic member 78 as compared to the contractive forces in the first elastic member 76. In some preferred embodiments, the elongation of the first elastic member 76 and the second elastic member 78 can be between about 125% to about 300%. However, it can be appreciated that the elongation amounts of the first and second elastic members 76, 78 can be outside of this preferable range. Furthermore, it is contemplated that the elongation amounts can be the same for the first elastic member 76 and the second elastic member 78.

As noted above and as illustrated in FIG. 4, the number of elastic materials can vary between the first elastic member 76 and the second elastic member 78. As one example, there can be more elastic materials forming the first elastic member 76 than the second elastic member 78. It is contemplated that there can be more elastic materials forming the second elastic member 78 than the first elastic member 76.

Furthermore, the spacing between adjacent elastic materials in the first elastic member 76 and the second elastic member 78 can vary between the first elastic member 76 and the second elastic member 78. For example, as illustrated in FIG. 4, the spacing between adjacent elastic materials forming the first elastic member 76 can be less than the spacing between adjacent elastic materials forming the second elastic member 78. In other embodiments, the spacing between adjacent elastic materials forming the first elastic member 76 can be the same as the spacing between adjacent elastic materials forming the second elastic member 78. In some embodiments, the spacing between adjacent elastic materials in the first elastic member 76 and the second elastic member 78 can be between about 1.0 mm to about 100.0 mm, preferably between about 2.0 mm and 50.0 mm, and more preferably between about 3.0 mm to about 25.0 mm. In one embodiment, the spacing between adjacent elastic materials in the first elastic member 76 and adjacent elastic materials in the second elastic member 78 can be about 5.0 mm.

The waist elastic member 50, 150, 250 as described herein can be of various sizes and shapes. In some preferable embodiments, the width of the waist elastic member 50, 150, 250 as measured in the lateral direction 32 can be between about 50 mm and about 850 mm. In some preferable embodiments, the length of the waist elastic member 50, 150, 250 as measured in the longitudinal direction 30 can be between about 25 mm and about 250 mm. Of course, it is contemplated that the waist elastic members 50, 150, 250 described herein can have a width and/or a length outside of these preferable ranges.

Fastening System:

In an embodiment, the absorbent article 10 can include a fastener system. The fastener system can include one or more back fasteners 95 and one or more front fasteners 96, with only one front fastener 96 being shown in FIGS. 1, 2, and 5. Portions of the fastener system may be included in the front waist region 12, rear waist region 14, or both.

The fastener system can be configured to secure the absorbent article 10 about the waist of the wearer in a fastened condition as shown in FIG. 1 and help maintain the absorbent article 10 in place during use. In an embodiment, the back fasteners 95 can include one or more materials bonded together to form a composite ear as is known in the art. For example, the composite fastener may be composed of a stretch component 97, a nonwoven carrier or hook base 98, and a fastening component 99.

Embodiments

Embodiment 1: An absorbent article including a front waist region, a rear waist region, and a crotch region, the crotch region extending between the front waist region and the rear waist region, the absorbent article further including a longitudinal axis and a lateral axis, the absorbent article comprising: an absorbent assembly including a bodyside liner, an outer cover, and an absorbent body disposed between the bodyside liner and the outer cover, the bodyside liner including a body facing surface and a garment facing surface, the outer cover including a body facing surface and a garment facing surface; and a waist elastic member disposed in one of the front waist region and the rear waist region, the waist elastic member including a body facing surface and a garment facing surface, the garment facing surface of the waist elastic member being bonded to one of the bodyside liner and the outer cover, the waist elastic member comprising: a carrier sheet including a first surface, a second surface opposite from the first surface, a first lateral edge, a second lateral edge, and opposing end edges; and a first elastic member and a second elastic member, the first elastic member and the second elastic member each including a first side and a second side, the second side being opposite from the first side, the first elastic member and the second elastic member each being coupled to the second surface of the carrier sheet; the carrier sheet being folded around the first elastic member such that a first portion of the carrier sheet is disposed on the first side of the first elastic member and a second portion of the carrier sheet is disposed on the second side of the first elastic member, the second portion of the carrier sheet including the first lateral edge, the carrier sheet being folded such that the first lateral edge does not longitudinally extend to or longitudinally overlap the second lateral edge.

Embodiment 2: An absorbent article including a front waist region, a rear waist region, and a crotch region, the crotch region extending between the front waist region and the rear waist region, the absorbent article further including a longitudinal axis and a lateral axis, the absorbent article comprising: an absorbent assembly including a bodyside liner, an outer cover, and an absorbent body disposed between the bodyside liner and the outer cover, the bodyside liner including a body facing surface and a garment facing surface, the outer cover including a body facing surface and a garment facing surface; and a waist elastic member bonded to the absorbent assembly and disposed in one of the front waist region and the rear waist region, the waist elastic member including a body facing surface and a garment facing surface, the garment facing surface of the waist elastic member being bonded to one of the bodyside liner and the outer cover, the waist elastic member comprising: a carrier sheet including a first surface, a second surface opposite from the first surface, a first lateral edge, a second lateral edge, and opposing end edges; a first laminating sheet including a first inner laminating surface, a first outer laminating surface opposite from the first inner laminating surface, a first edge, a second edge opposite the first edge, and opposing end edges, the first laminating sheet configured such that the first edge of the first laminating sheet substantially longitudinally aligns with the first lateral edge of the carrier sheet and the second edge of the first laminating sheet does not longitudinally extend to or overlap with the second lateral edge of the carrier sheet; and a first elastic member and a second elastic member, the first elastic member and the second elastic member each including a first side and a second side, the second side being opposite from the first side, the carrier sheet being disposed on the first side of the first elastic member and the first side of the second elastic member, the first elastic member being disposed between the second surface of the carrier sheet and the first inner laminating surface of the first laminating sheet.

Embodiment 3: An absorbent article including a front waist region, a rear waist region, and a crotch region, the crotch region extending between the front waist region and the rear waist region, the absorbent article further including a longitudinal axis and a lateral axis, the absorbent article comprising: an absorbent assembly including a bodyside liner, an outer cover, and an absorbent body disposed between the bodyside liner and the outer cover, the bodyside liner including a body facing surface and a garment facing surface, the outer cover including a body facing surface and a garment facing surface; and a waist elastic member disposed in one of the front waist region and the rear waist region, the waist elastic member including a body facing surface and a garment facing surface, the garment facing surface of the waist elastic member being bonded to one of the bodyside liner and the outer cover, the waist elastic member comprising: a first longitudinal zone, a second longitudinal zone, and a middle longitudinal zone in between the first longitudinal zone and the second longitudinal zone, wherein the first longitudinal zone includes a first elastic member disposed between two layers of material, the second longitudinal zone includes a second elastic member disposed between two layers of material, and the middle longitudinal zone includes less layers of material than each of the first longitudinal zone and the second longitudinal zone.

Embodiment 4: The absorbent article of embodiment 1, wherein the carrier sheet is folded around the second elastic member such that the first portion of the carrier sheet is disposed on the first side of the second elastic member and a third portion of the carrier sheet is disposed on the second side of the second elastic member, the third portion of the carrier sheet including the second lateral edge, the carrier sheet being folded such that the second lateral edge does not longitudinal extend to or longitudinally overlap the first lateral edge.

Embodiment 5: The absorbent article of embodiment 2, wherein the waist elastic member further comprises a second laminating sheet including a second inner laminating surface, a second outer laminating surface opposite from the second inner laminating surface, a first edge, a second edge opposite the first edge, and opposing end edges, the second elastic member being disposed between the second surface of the carrier sheet and the second inner laminating surface of the second laminating sheet, the second laminating sheet configured such that the second edge of the second laminating sheet substantially longitudinally aligns with the second lateral edge of the carrier sheet and the first edge of the second laminating sheet does not longitudinally extend to or overlap with the second edge of the first laminating sheet.

Embodiment 6: The absorbent article of embodiment 4, wherein the second surface of the carrier sheet in the second portion of the carrier sheet near the first lateral edge is bonded to the second surface of the carrier sheet in the first portion of the carrier sheet between the first elastic member and the second elastic member.

Embodiment 7: The absorbent article of embodiment 6, wherein the second surface of the carrier sheet in the third portion of the carrier sheet near the second lateral edge is bonded to the second surface of the carrier sheet in the first portion of the carrier sheet between the first elastic member and the second elastic member.

Embodiment 8: The absorbent article of any one of the preceding embodiments, wherein substantially all of the garment facing surface of the waist elastic member is bonded to the absorbent assembly.

Embodiment 9: The absorbent article of any one of embodiments 1-7, wherein there is a longitudinal gap between the first elastic member and the second elastic member, and the garment facing surface of the waist elastic member is bonded to the absorbent assembly such that there is a central unbonded region.

Embodiment 10: The absorbent article of embodiment 9, wherein the central unbonded region is aligned with the longitudinal gap between the first elastic member and the second elastic member.

Embodiment 11: The absorbent article of embodiment 3, wherein the middle longitudinal zone does not include an elastic member.

Embodiment 12: The absorbent article of embodiment 11, wherein a carrier sheet forms the two layers of material in the first longitudinal zone and the second longitudinal zone by being folded such that a first portion of the carrier sheet is disposed on a first side of the first elastic element and the first side of the second elastic element, a second portion of the carrier sheet is disposed on a second side of the first elastic element, and a third portion of the carrier sheet is disposed on a second side of the second elastic element, the carrier sheet folded such that the second portion and the third portion of the carrier sheet are not within the middle longitudinal zone of the waist elastic member.

Embodiment 13: The absorbent article of embodiment 11, wherein a carrier sheet forms a first layer of material in the first longitudinal zone, the second longitudinal zone, and the middle longitudinal zone, a first laminating sheet forms a second layer of material in the first longitudinal zone, and a second laminating sheet forms a second layer of material in the second longitudinal zone.

Embodiment 14: The absorbent article of any one of the preceding embodiments, wherein the waist elastic member is disposed between the garment facing surface of the bodyside liner and the body facing surface of the outer cover.

Embodiment 15: The absorbent article of any one of embodiments 1-13, further comprising: a pair of containment flaps bonded to the bodyside liner; wherein the garment facing surface of the waist elastic member is bonded to the body facing side of the bodyside liner and is disposed between the containment flaps and the body facing side of the bodyside liner.

Embodiment 16: The absorbent article of any one of embodiments 1-13, further comprising: a pair of containment flaps bonded to the bodyside liner; wherein the garment facing surface of the waist elastic member is bonded to the body facing side of the bodyside liner and the pair of containment flaps.

Embodiment 17: The absorbent article of any one of the preceding embodiments, wherein the waist elastic member is disposed in the rear waist region.

Embodiment 18: The absorbent article of any one of the preceding embodiments, wherein the first elastic member and the second elastic member each include at least two elastic strands.

Embodiment 19: The absorbent article of embodiment 18, wherein there is a longitudinal gap between the first elastic member and the second elastic member, the longitudinal gap being greater than a longitudinal spacing between the at least two elastic strands in the first elastic member and greater than a longitudinal spacing between the at least two elastic strands in the second elastic member.

Embodiment 20: The absorbent article of any one of the preceding embodiments, wherein a decitex of the first elastic member is different than a decitex of the second elastic member.

Embodiment 21: The absorbent article of embodiment 20, wherein the decitex of the second elastic member is greater than the decitex of the first elastic member.

Embodiment 22: The absorbent article of any one of the preceding embodiments, wherein an elongation amount of the first elastic member is different than an elongation amount of the second elastic member.

Embodiment 23: The absorbent article of embodiment 22, wherein the elongation amount of the second elastic member is greater than the elongation amount of the first elastic member.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a front waist region, a rear waist region, and a crotch region, the crotch region extending between the front waist region and the rear waist region, the absorbent article further including a longitudinal axis and a lateral axis, the absorbent article comprising:
   an absorbent assembly including a bodyside liner, an outer cover, and an absorbent body disposed between the bodyside liner and the outer cover, the bodyside liner including a body facing surface and a garment facing surface, the outer cover including a body facing surface and a garment facing surface; and
   a waist elastic member disposed in one of the front waist region and the rear waist region, the waist elastic member including a body facing surface and a garment facing surface, the garment facing surface of the waist elastic member being bonded to one of the bodyside liner and the outer cover, the waist elastic member comprising:
      a carrier sheet including a first surface, a second surface opposite from the first surface, a first lateral edge, a second lateral edge, and opposing end edges; and
      a first elastic member and a second elastic member, the first elastic member and the second elastic member each including a first side and a second side, the second side being opposite from the first side, the first elastic member and the second elastic member each being coupled to the second surface of the carrier sheet;
      the carrier sheet being folded around the first elastic member such that a first portion of the carrier sheet is disposed on the first side of the first elastic member and a second portion of the carrier sheet is disposed on the second side of the first elastic member, the second portion of the carrier sheet including the first lateral edge, the carrier sheet being further folded around the second elastic member such that the first portion of the carrier sheet is disposed on the first side of the second elastic member and a third portion of the carrier sheet is disposed on the second side of the second elastic member, the third portion of the carrier sheet including the second lateral edge, and the carrier sheet being folded such that the first lateral edge does not longitudinally extend to or longitudinally overlap the second lateral edge, and
      wherein the second surface of the carrier sheet between the first elastic member and the second elastic member is free of adhesive.

2. The absorbent article of claim 1, wherein the second surface of the carrier sheet in the second portion of the carrier sheet near the first lateral edge is bonded to the second surface of the carrier sheet in the first portion of the carrier sheet between the first elastic member and the second elastic member.

3. The absorbent article of claim 2, wherein the second surface of the carrier sheet in the third portion of the carrier sheet near the second lateral edge is bonded to the second surface of the carrier sheet in the first portion of the carrier sheet between the first elastic member and the second elastic member.

4. The absorbent article of claim 1, wherein substantially all of the garment facing surface of the waist elastic member is bonded to the absorbent assembly.

5. The absorbent article of claim 1, wherein there is a longitudinal gap between the first elastic member and the second elastic member, and the garment facing surface of the waist elastic member is bonded to the absorbent assembly such that there is a central unbonded region.

6. The absorbent article of claim 5, wherein the central unbonded region is aligned with the longitudinal gap between the first elastic member and the second elastic member.

7. The absorbent article of claim 1, wherein the waist elastic member is disposed between the garment facing surface of the bodyside liner and the body facing surface of the outer cover.

8. The absorbent article of claim 1, further comprising:
   a pair of containment flaps bonded to the bodyside liner;
   wherein the garment facing surface of the waist elastic member is bonded to the body facing side of the bodyside liner and is disposed between the containment flaps and the body facing side of the bodyside liner.

9. The absorbent article of claim 1, further comprising:
   a pair of containment flaps bonded to the bodyside liner;
   wherein the garment facing surface of the waist elastic member is bonded to the body facing side of the bodyside liner and the pair of containment flaps.

10. The absorbent article of claim 1, wherein a decitex of the first elastic member is different than a decitex of the second elastic member.

11. The absorbent article of claim 10, wherein the decitex of the second elastic member is greater than the decitex of the first elastic member.

12. The absorbent article of claim 1, wherein an elongation amount of the first elastic member is different than an elongation amount of the second elastic member.

13. The absorbent article of claim 12, wherein the elongation amount of the second elastic member is greater than the elongation amount of the first elastic member.

14. An absorbent article including a front waist region, a rear waist region, and a crotch region, the crotch region extending between the front waist region and the rear waist region, the absorbent article further including a longitudinal axis and a lateral axis, the absorbent article comprising:
   an absorbent assembly including a bodyside liner, an outer cover, and an absorbent body disposed between the bodyside liner and the outer cover, the bodyside liner including a body facing surface and a garment facing surface, the outer cover including a body facing surface and a garment facing surface; and
   a waist elastic member bonded to the absorbent assembly and disposed in one of the front waist region and the rear waist region, the waist elastic member including a body facing surface and a garment facing surface, the garment facing surface of the waist elastic member being bonded to one of the bodyside liner and the outer cover, the waist elastic member comprising:
      a carrier sheet including a first surface, a second surface opposite from the first surface, a first lateral edge, a second lateral edge, and opposing end edges;
      a first laminating sheet including a first inner laminating surface, a first outer laminating surface opposite from the first inner laminating surface, a first edge, a second edge opposite the first edge, and opposing end edges, the first laminating sheet configured such that the first edge of the first laminating sheet substantially longitudinally aligns with the first lateral edge of the carrier sheet and the second edge of the first laminating sheet does not longitudinally extend to or overlap with the second lateral edge of the carrier sheet; and
      a first elastic member and a second elastic member, the first elastic member and the second elastic member each including a first side and a second side, the second side being opposite from the first side, the carrier sheet being disposed on the first side of the first elastic member and the first side of the second elastic member, the first elastic member being disposed between the second surface of the carrier sheet and the first inner laminating surface of the first laminating sheet.

15. The absorbent article of claim 14, wherein the waist elastic member further comprises a second laminating sheet including a second inner laminating surface, a second outer laminating surface opposite from the second inner laminating surface, a first edge, a second edge opposite the first edge, and opposing end edges, the second elastic member being disposed between the second surface of the carrier sheet and the second inner laminating surface of the second laminating sheet, the second laminating sheet configured such that the second edge of the second laminating sheet substantially longitudinally aligns with the second lateral edge of the carrier sheet and the first edge of the second laminating sheet does not longitudinally extend to or overlap with the second edge of the first laminating sheet.

16. The absorbent article of claim 14, wherein the waist elastic member is disposed in the rear waist region.

17. The absorbent article of claim 14, wherein the first elastic member and the second elastic member each include at least two elastic strands.

18. The absorbent article of claim 17, wherein there is a longitudinal gap between the first elastic member and the second elastic member, the longitudinal gap being greater than a longitudinal spacing between the at least two elastic strands in the first elastic member and greater than a longitudinal spacing between the at least two elastic strands in the second elastic member.

19. An absorbent article including a front waist region, a rear waist region, and a crotch region, the crotch region extending between the front waist region and the rear waist region, the absorbent article further including a longitudinal axis and a lateral axis, the absorbent article comprising:
an absorbent assembly including a bodyside liner, an outer cover, and an absorbent body disposed between the bodyside liner and the outer cover, the bodyside liner including a body facing surface and a garment facing surface, the outer cover including a body facing surface and a garment facing surface; and
a waist elastic member disposed in one of the front waist region and the rear waist region, the waist elastic member including a body facing surface and a garment facing surface, the garment facing surface of the waist elastic member being bonded to one of the bodyside liner and the outer cover, the waist elastic member comprising:
a first longitudinal zone, a second longitudinal zone, and a middle longitudinal zone in between the first longitudinal zone and the second longitudinal zone, wherein the first longitudinal zone includes a first elastic member disposed between two layers of material of the waist elastic member, the second longitudinal zone includes a second elastic member disposed between two layers of material of the waist elastic member, and the middle longitudinal zone includes less layers of material of the waist elastic member than each of the first longitudinal zone and the second longitudinal zone and the middle longitudinal zone further being free of adhesive.

20. The absorbent article of claim 19, wherein the middle longitudinal zone does not include an elastic member.

21. The absorbent article of claim 20, wherein a carrier sheet forms the two layers of material in the first longitudinal zone and the second longitudinal zone by being folded such that a first portion of the carrier sheet is disposed on a first side of the first elastic element and the first side of the second elastic element, a second portion of the carrier sheet is disposed on a second side of the first elastic element, and a third portion of the carrier sheet is disposed on a second side of the second elastic element, the carrier sheet folded such that the second portion and the third portion of the carrier sheet are not within the middle longitudinal zone of the waist elastic member.

22. The absorbent article of claim 20, wherein a carrier sheet forms a first layer of material in the first longitudinal zone, the second longitudinal zone, and the middle longitudinal zone, a first laminating sheet forms a second layer of material in the first longitudinal zone, and a second laminating sheet forms a second layer of material in the second longitudinal zone.

* * * * *